United States Patent [19]

Thomas et al.

[11] 4,441,769

[45] Apr. 10, 1984

[54] LENS DISINFECTING UNIT

[75] Inventors: Michael D. Thomas; Francis E. Ryder, both of Arab, Ala.

[73] Assignee: Ryder International Corporation, Arab, Ala.

[21] Appl. No.: 369,413

[22] Filed: Apr. 19, 1982

[51] Int. Cl.³ .................... A47B 47/00; B65D 41/16; B65D 41/18
[52] U.S. Cl. .................... 312/270; 220/306; 220/337; 312/293; 312/327
[58] Field of Search ............ 312/257 A, 257 SM, 327, 312/328, 284, 253, 293; 206/5.1, 6; 220/306, 337, 334

[56] References Cited

U.S. PATENT DOCUMENTS

| | | | |
|---|---|---|---|
| 3,563,370 | 2/1971 | Nozette et al. | 220/306 |
| 4,157,600 | 6/1979 | Thomas | 16/169 |
| 4,214,797 | 7/1980 | Borresen et al. | 220/306 |
| 4,307,289 | 12/1981 | Thomas et al. | 219/521 |
| 4,314,637 | 2/1982 | Posso | 220/306 |
| 4,366,915 | 1/1983 | Seidler | 220/306 |

FOREIGN PATENT DOCUMENTS 442364  2/1936  United Kingdom ............... 220/337

Primary Examiner—William E. Lyddane
Assistant Examiner—Thomas A. Rendos
Attorney, Agent, or Firm—Trexler, Bushnell & Wolters, Ltd.

[57] ABSTRACT

A lens disinfecting unit comprises a housing with adjacent compartments separated by a barrier wall. One compartment is adapted to receive the lens case for heating while the other compartment contains the heater and related circuitry. The barrier wall includes a heat sink which is insert-molded into the barrier wall to provide a water-tight seal such spilled liquid cannot leak from the lens case compartment to the heater compartment. The casing for the unit is made up of sections permitting sequential assembly, namely, two members are employed, one being a lid pivotally mounted over the heating well and the other being snap-fitted over the compartment containing the circuitry; and a third member serves to maintain the other two members in captive relationship.

2 Claims, 8 Drawing Figures

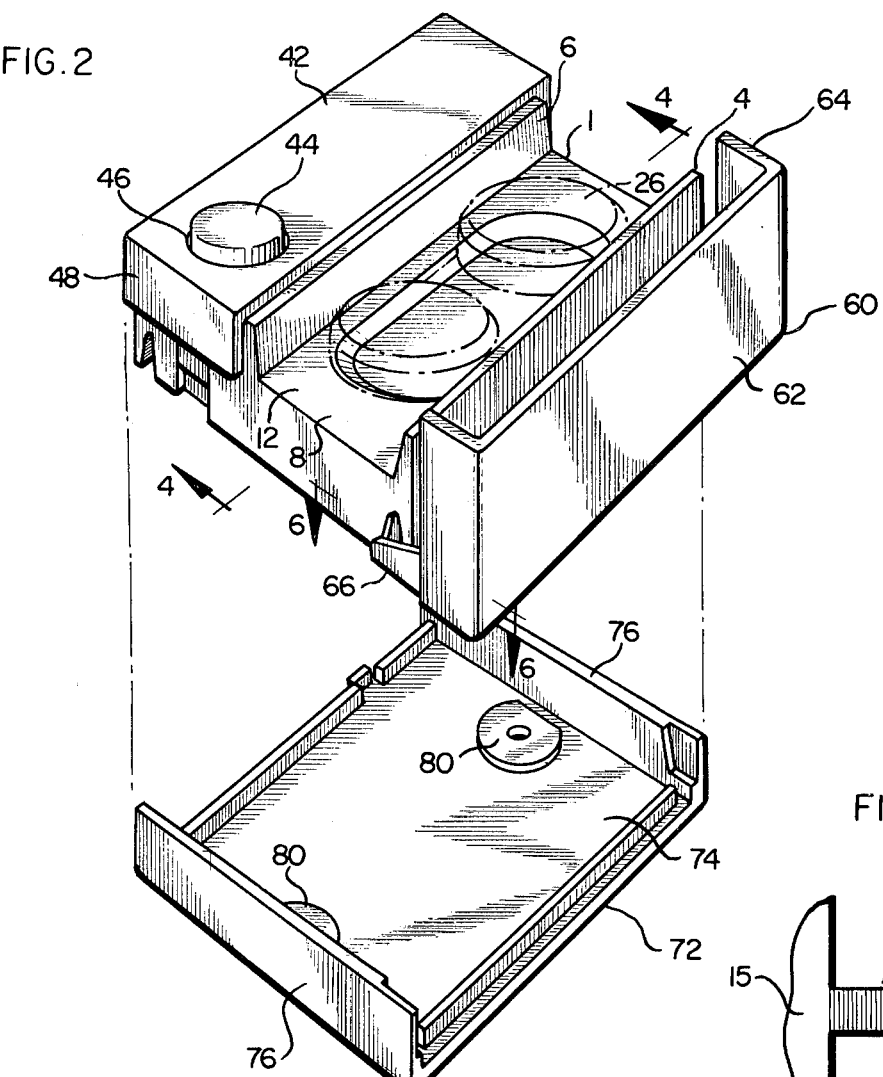
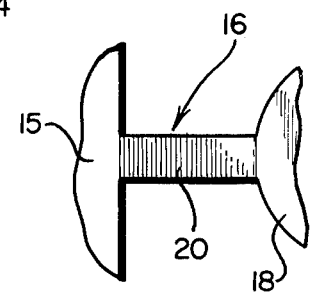
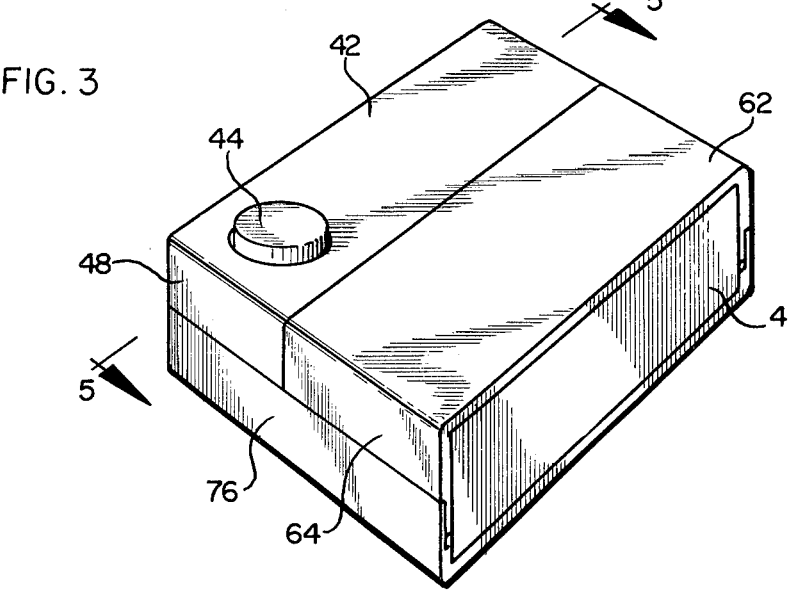

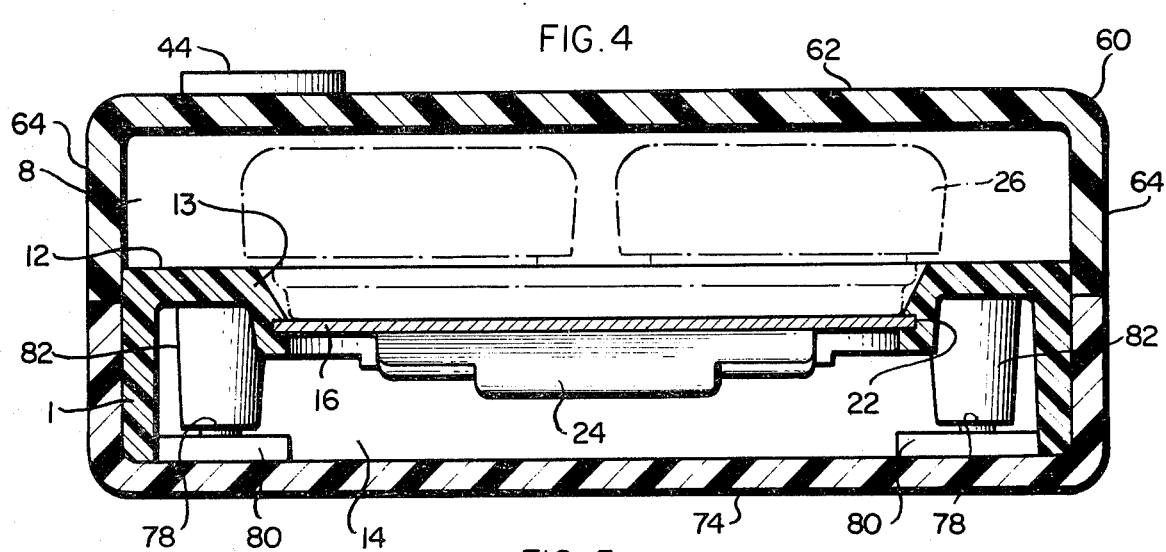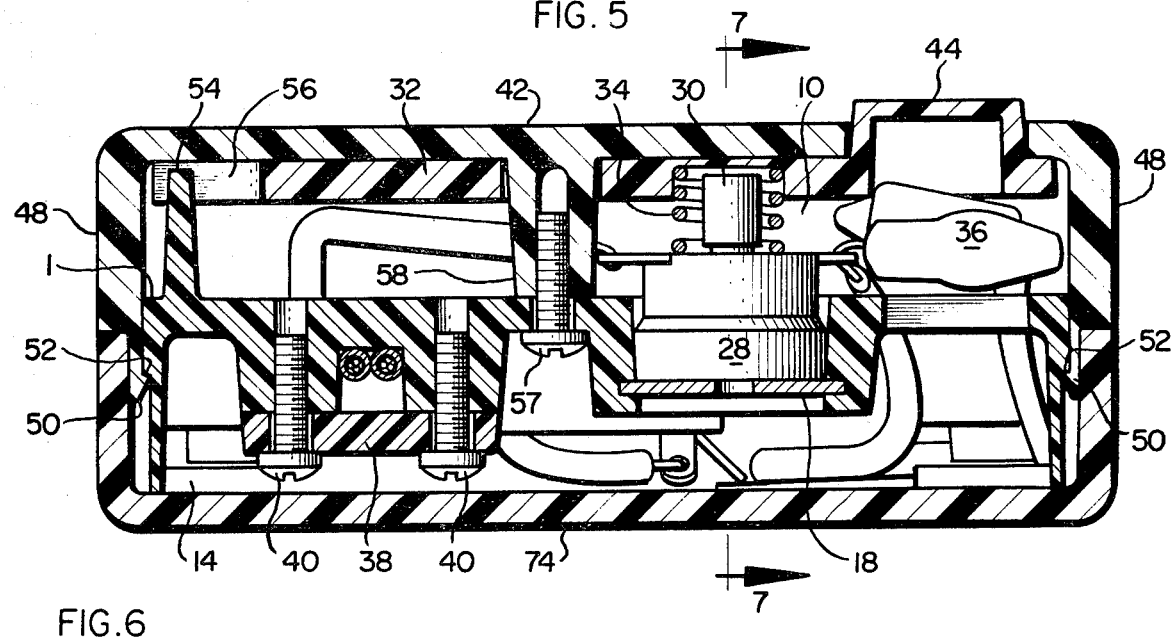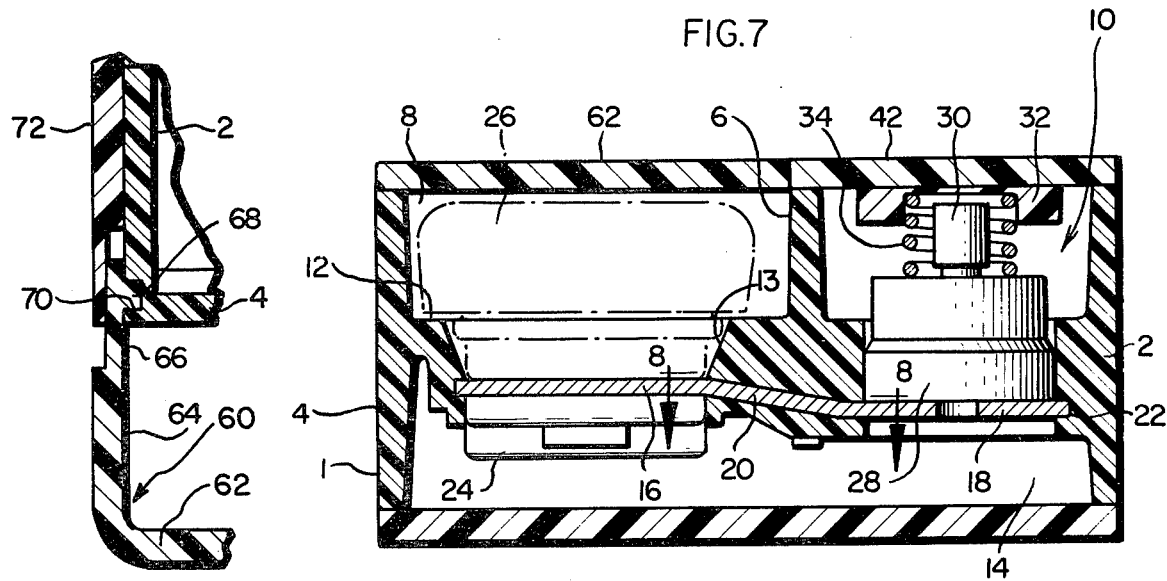

LENS DISINFECTING UNIT

BACKGROUND OF THE INVENTION

This invention relates to new and useful improvements in disinfectors for contact lenses and similar small objects, and most particulary to an improved housing construction for said disinfectors.

In order to prevent the wearer of contact lenses from becoming infected as a result of accumulation of bacteria on the lenses the lenses must be regularly disinfected. Such disinfecting is usually carried out by heating the lens in a saline solution to a sufficient temperature and for a proper period of time. Typically during the disinfecting cycle the range of temperatures to which the lenses are subjected should be in the order of 60° C. to 80° C.

It is known to provide contact lens disinfecting units which are electrically operated in that they contain electrical heaters which operate from a 115 volt electrical source. In such units a lens case containing the saline solution may be introduced into a heating chamber of the unit whereupon the unit is activated to run through the disinfecting cycle. The electrical heater heats the lens case either directly or through the medium of a heat sink, but in either event there is the possibility of spillage of the saline solution during the procedure. Sometimes this spillage of saline solution will run into the lens case heating compartment or well and leak therefrom onto the heater or wiring or other electrical components within the unit. As a result, corrosion of the electrical components and possible short-circuiting may result.

Many such portable units are assembled essentially by hand, and as a result the cost of production of these units tends to be labor intensive. Accordingly, it is desirable to reduce the assembly costs of these disinfecting units while at the same time maintaining proper standards of durability and safety of operation.

GENERAL OBJECTS AND SUMMARY OF THE INVENTION

An object of this invention is to provide a contact lens disinfecting unit in which a heat transfer medium or heat sink as it is called is utilized to transfer heat from an electrical heater to the lens case and wherein the heat sink is insert-molded into the housing of the unit so as to provide a liquid tight barrier for the lens case heating well. Such an arrangement prevents corrosive liquids which have accidentally entered the heating well from leaking into the interior of the unit and possibly damaging electrical components therein.

A further object of this invention is to provide a housing construction or casing for a disinfecting unit of the type stated, or the like, which is relatively easy to assemble by a sequential method in which successive parts of the casing are utilized to retain in place the preceding parts while at the same time providing a relatively neat and compact structure which is highly portable and can be carried in a purse or coat pocket. Moreover, the unit may be assembled without excessive use of screws or like fasteners and wherein the several members of the casing may be assembled without the use of tools.

In accordance with the immediately foregoing objects, the casing is comprised of a housing or main unit which contains the heater, the heat transfer medium or heat sink, and related circuitry. Two covers are employed, one being pivotally mounted over the heating well for the lens case and the other being snap-fitted over the compartment containing the thermostat, the reset switch and related circuitry. The bottom part of the main unit is closed by a base member which serves to maintain the cover in a captive pivotally mounted relationship and also serves to prevent removal of the snap-fitted cover.

More particularly, the disinfecting unit comprises a housing having a first compartment and an adjacent second compartment, means forming a liquid-tight seal between said compartments, means in said first compartment forming a support for receiving a lens case, a heat-transmitting medium presented to said first compartment for transmission of heat to the lens case, electric circuit means including a switch and a heater in said second compartment, a switch actuator in said second compartment, a cover for a part of said second compartment in which the actuator is located, interfitting means forming an assembly fit between said cover and said housing, a base for covering another part of said second compartment and having means for covering said interfitting means, and a lid pivotally mounted on said housing for disposition over said first compartment, the pivotal mounting of said lid being overlaid and held captive by said base.

In another aspect of the invention the disinfecting unit comprises a housing having a first compartment and an adjacent second compartment, a plastic wall forming a barrier between said compartment, one of said compartments containing an electric heater and electrical conductors leading thereto, the other of said compartments being shaped to receive the lens case, said barrier wall having an opening, a metallic heat sink in thermal conductive relationship with said heater and being exposed to said first compartment for contact with the lens case, the heat sink being insert-molded with the plastic of the barrier wall to enclose the periphery of said heat sink and form a fluid-tight seal at said opening.

BRIEF DESCRIPTION OF THE FIGURES

FIG. 2 is an exploded perspective view showing the unit partially assembled and with the lid for the lens case compartment being shown in the open position;

FIG. 3 is a perspective view of the assembled unit with the lid in its closed position;

FIG. 4 is a sectional view taken approximately along lines 4—4 of FIG. 2 but with the unit shown in assembled position;

FIG. 5 is a sectional view taken along line 5—5 of FIG. 3;

FIG. 6 is a fragmentary sectional view taken along line 6—6 of FIG. 2;

FIG. 7 is a sectional view taken along line 7—7 of FIG. 5 and;

FIG. 8 is a partial sectional view taken along line 8—8 of FIG. 7, and illustrating the neck portion interconnecting the two distinct heat sink sections of the illustrated embodiment.

DETAILED DESCRIPTION

Figure 1:
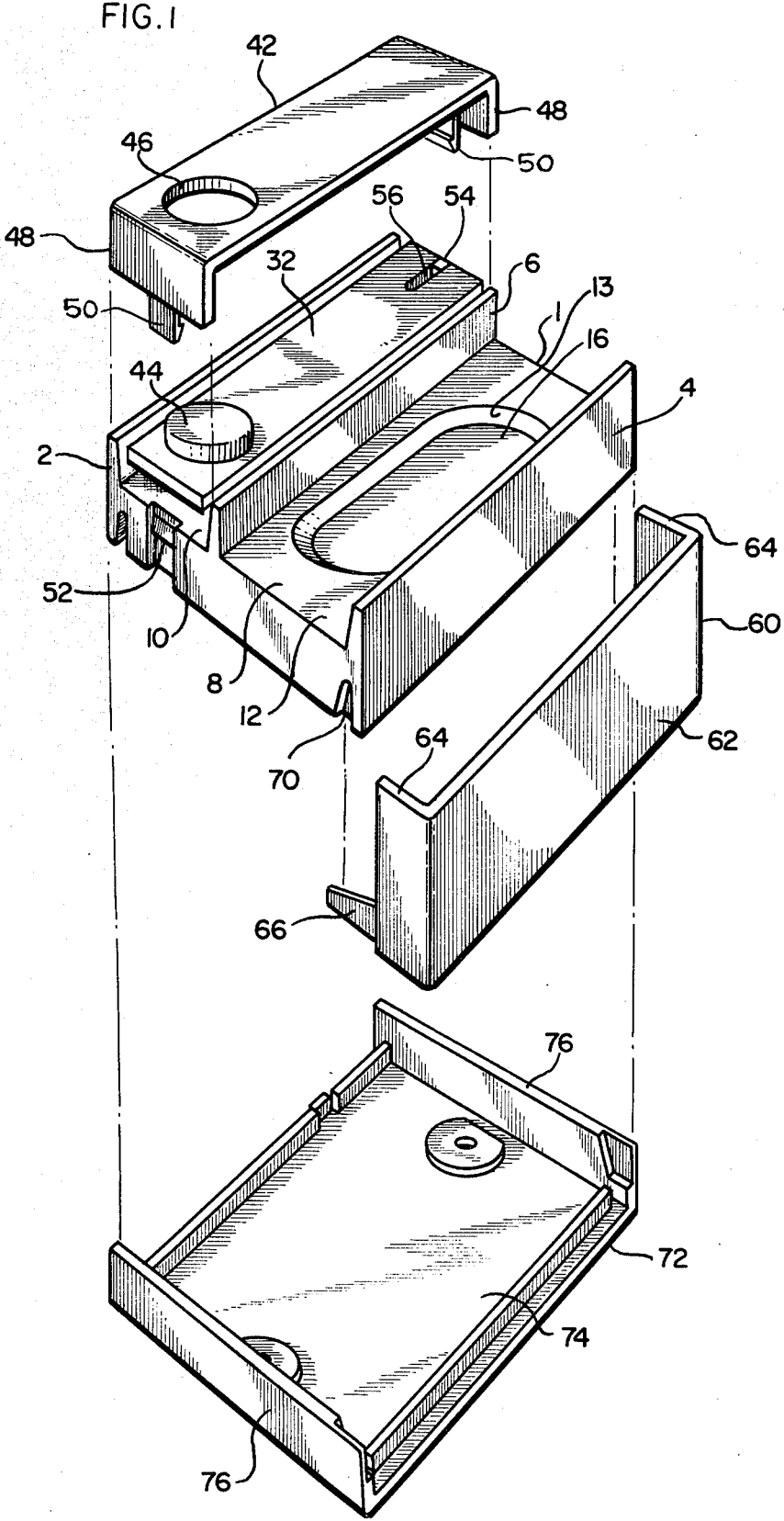
FIG. 1 is an exploded perspective view of a lens-disinfecting unit constructed in accordance with and embodying the present invention.

Referring now in more detail to the drawing, which illustrates a preferred embodiment of the present invention, the lens disinfecting unit comprises a housing 1 formed of a suitable molded plastic material. The housing 1 includes opposed parallel walls 2, 4 and an intermediate wall 6. The housing 1 is so constructed as to provide a first or lens case-receiving compartment or chamber 8 and a second compartment 10. The first compartment 8 is defined by means including the walls 4, 6 and a lens case supporting floor 12 including a well 13 for reception of a lens case. The second compartment is defined by means including the walls 2, 6 and also by the back-side or bottom chamber 14 of the housing which contains electrical components of the unit, as will be more fully described and as seen in FIGS. 4, 5 and 7. The two compartments 8, 10 are essentially isolated from each other sufficiently to prevent leakage of fluids slipped into the compartment 8 from entering the compartment 10.

A heat-transmitting element or metallic heat sink 16 is insert molded in the housing 1 and provides a floor or base for the well 13. That is to say, that the metallic heat sink blank 16 is disposed in the mold for the housing, and the plastic material forming the housing 1 is molded about the heat sink blank to provide an integral structural unit. This heat sink 16 may be of a suitable material with a high heat conductivity, such as anodized aluminum. The main portion 15 of the heat sink 16 is exposed to and forms part of the floor 12 of the lens case receiving compartment 1. An additional or smaller portion 18 of the heat sink is laterally offset from the main portion and is joined thereto by a narrow strip or neck portion FIG. 8, this smaller portion 18 extending into the second compartment. As best seen in FIGS. 4, 5 and 7 the insert molding operation completely encloses the periphery 22 of the heat sink 16 so that a fluid tight seal is formed between the plastic and the metal of the heat sink. This is especially important at the floor 12 because fluid accidentally deposited on the floor 12 cannot enter the interior of housing 1 and thus any danger of damage to the components in the chamber 14 is precluded. The insert molding technique is positive and effective, and eliminates the need for special gaskets and like sealing structure between the heat sink 16 and the housing 1.

Within the chamber 14 and disposed against the bottom side of the heat sink 16 is an electric heater 24 which transmits heat directly to the portion of the heat sink 16 that constitutes part of the floor 12 for well 13. This heat in turn is directly transmitted to a lens case 26 shown in broken lines in FIG. 4 and which seats directly against the exposed surface of the heat sink 16. In the chamber 10 there is positioned a thermostatic switch 28 of conventional construction and which seats on the heat sink portion 18. This thermostatic switch 28 thus receives heat from the heat sink through the narrow strip or necked down portion 20, which insures that the major portion 15 of heat sink 16 is heated to a temperature level at least equal to or greater than that of the smaller portion 18. The thermostatic switch 28 also includes an upwardly projecting reset button 30 that is actuated by a reset lever 32. The reset lever 32 is biased upwardly from the reset button 30 by a spring 34.

The circuitry for wiring the heater 24 and the thermostatic switch 28 is conventional, and portions of the wiring are shown in FIG. 5. The circuit may include a pilot lamp 36; and the wires may be retained in a conventional manner by a strain relief clamp 38 (FIG. 5), the latter being secured to the housing 1 by screws 40.

Attention is now directed to the general construction of the overall casing which provides ease of assembly by sequential steps with successive parts of the casing being utilized to retain in place preceding parts. In this regard, the preceding discussion was directed primarily to the internal construction of the overall disinfector unit, while the following discussion is concerned with the outer structural components of the casing, which give rise to the objects and advantages discussed above.

Provided for closing off the portion of the compartment 10 defined by the walls 2, 6 is a plastic cover 42 which furthermore provides a retainer for the reset lever 32. The reset lever 32 has a raised bead or button 44 that projects through an opening 46 near one end of the cover 42. The cover 42 is substantially as wide as the distance between the walls 2, 6. At the opposite ends of the cover 42 there are downwardly turned end flanges 48, 48 each having a resilient spring fingers or hooks 50, 50 (FIG. 5) which snap-fit over downwardly presented shoulders, 52, 52 on the housing 1. Such an arrangement locks the cover 42 to the housing 1 and also causes an upstanding post 54 on the housing to enter an elongated slot 56 at the end of the lever 32 that is opposite to the button 44 and form a fulcrum for the lever 32. Optionally, a screw 57 may project through the housing and be threaded into a boss 58 on the cover 42 further to insure assembly of the cover with the housing.

After the cover 42 has been assembled to the housing as described above, a plastic lid 60 is pivotally mounted to the housing. This lid 60 comprises a top wall 62 and side walls 64, each of the latter including a pivot arm 66. As best seen in FIGS. 1 and 6 each pivot arm 66 has a bead 68 that rides in an elongated vertical slot 70 in the housing 1. The slot opens downwardly to permit entry of the bead 68 therein whereupon the lid is raised to permit entry of the bead 68 therein whereupon the lid is raised to move the bead 68 to the upper end of the slot 70. The lid 62 may thus be pivoted on the housing to and from the open position shown in FIG. 2 to the closed position of FIG. 3, wherein the cover overlies the lens case receiving compartment 8.

After assembly of the cover 42 and the lid 62, a base member 72 is assembled with the remaining parts. This base 72 has a bottom wall 74 and opposed parallel side sections 76, 76. The side sections 76 fit over the housing 1 and cover or overlie the hooks or spring fingers 50, 50. The overlap of the sections 76 with respect to spring fingers or hooks 50, 50 serves to prevent hooks 50, 50 from becoming disengaged from the shoulder 52 and thus precludes inadvertant disassembly. The side sections 76, 76 also cover portions of the pivot arms 66 to retain the arms 66 in captive, pivot-forming relationship within the slots 70 and thereby prevent separation of the lid 60 from the housing 1. Moreover, as best seen in FIG. 3, when the unit is closed the flange 48 and the walls 64, 76 are in substantially flush relationship to define an additional pair of opposed walls of the unit. The base 72 may be secured to the housing 1 by screws 78, 78 (FIG. 4) which pass through bosses 80 on the bottom wall 74 and are threaded into depending bosses 82, 82 on the housing 1. Accordingly, there has been disclosed and described a preferred embodiment of the invention. It is envisioned that those skilled in the art and possessed of this disclosure may devise various modifications to the preferred, illustrated embodiment without departing from the spirit and scope of the invention as defined by the claims appended hereto.

The invention is claimed as follows:

1. A housing construction for a lens disinfecting unit or the like, said housing having a pair of spaced walls forming opposed walls of the housing; a cover for part of said housing, interfitting means on said cover and housing for retaining the housing and cover assembled, a lid in pivotal connection with the housing for closing another part of the housing, and a base for covering a further part of said housing, said base overlying said interfitting means and said pivotal connection in such manner as to prevent separation of the lid and cover from said housing; the cover, the base, and the lid when closed cooperating to define two additional sets of opposed walls for the housing that cooperate with the first-mentioned set of opposed walls to form an enclosure.

2. A housing construction according to claim 1 in which said interfitting means is a snap fit, said pivotal mounting comprises a pivot pin and a pivot pin slot, said lid and cover are side-by-side and at one side of the housing when the lid is in closed position, and said base is at a side of said housing that is opposite to said one side.

* * * * *